(12) United States Patent
Murray et al.

(10) Patent No.: US 7,390,090 B2
(45) Date of Patent: Jun. 24, 2008

(54) OCULAR MEASUREMENT APPARATUS AND METHOD

(75) Inventors: Ian Murray, 41 Pine Road, Didsbury, Manchester, M20 6UZ (GB); David Carden, 9 Woodhey Grove, Syke, Rochdale, Lancs, OL12 9TY (GB)

(73) Assignees: Ian Murray, Didsbury (GB); David Carden, Rochdale (GB)

( * ) Notice: Subject to any disclaimer, the term of this patent is extended or adjusted under 35 U.S.C. 154(b) by 261 days.

(21) Appl. No.: 11/402,260

(22) Filed: Apr. 12, 2006

(65) Prior Publication Data

US 2006/0227290 A1    Oct. 12, 2006

(30) Foreign Application Priority Data

Apr. 12, 2005   (GB)   .................. 0507430.7

(51) Int. Cl.
*A61B 3/04*   (2006.01)
*A61B 3/02*   (2006.01)

(52) U.S. Cl. .................. 351/237; 351/239; 351/243; 351/246

(58) Field of Classification Search .................. 351/200, 351/201, 222, 237, 239, 243, 246

See application file for complete search history.

(56) References Cited

U.S. PATENT DOCUMENTS

| 4,511,228 | A | * | 4/1985 | von Gierke et al. | 351/243 |
| 4,940,323 | A | * | 7/1990 | Downing | 351/203 |
| 5,381,195 | A | * | 1/1995 | Rootzen et al. | 351/222 |
| 6,017,122 | A |   | 1/2000 | Bone et al. | 351/221 |
| 6,315,412 | B1 |   | 11/2001 | Snodderly et al. | 351/200 |

* cited by examiner

*Primary Examiner*—Huy K Mai
(74) *Attorney, Agent, or Firm*—Pillsbury Winthrop Shaw Pittman LLP (57) ABSTRACT

According to an aspect of the present invention, there is provided a measurement apparatus for measuring a property of an eye of a subject, having a target arranged to be viewed by the subject, the target including a first light and a second light arranged to undergo a modulation in anti-phase, the modulation decreasing from an initial modulation frequency at which an initial flicker of the first light and second light is not perceivable by the subject; and an indication device allowing the subject to indicate when a flicker is perceived, the modulation frequency at which the subject indicates that the flicker is perceived being defined as a threshold modulation frequency.

36 Claims, 7 Drawing Sheets

OCULAR MEASUREMENT APPARATUS AND METHOD

RELATED APPLICATIONS

This application claims the priority of British Patent Application No. GB 0507430.7, filed Apr. 12, 2005, the entire contents of which is hereby incorporated by reference.

FIELD

The present invention relates to an ocular measurement apparatus and method, and more specifically to an apparatus for and method of measuring a property of an eye of a subject.

BACKGROUND

The eye is an extremely sensitive organ. The high sensitivity can be used to accurately determine a wide range of properties of the eye, for example the eye's temporal, spatial and chromatic performance. In turn, these and other properties can yield, directly or indirectly, information pertaining toward the health of the eye.

Due to the importance of the eye and the associated sense of sight, it is not unsurprising that diagnosis and treatment of problems with the eye is the subject of vast amounts of research and development. Of particular interest to many researchers is the retina.

The parts of a human or animal body involved in the processing of light, or 'the sense of sight' are, amongst others: a lens, a retina, an optic nerve and a brain.

The retina is the part of the eye upon which light impinges after passing through the lens. The retina is a thin membrane inside the wall of the eye, and comprises a large number of light (and colour) sensitive cells, or 'photoreceptors'. The retina transforms the light transmitted by the lens into chemical and electrical signals that are sent to the brain via the optic nerve. Maintenance of the health of the retina is crucial to maintaining a healthy eye and thus good sight.

One way of determining the health of the eye is to determine the optical density of one or many of the various constituent components of the retina. One such component is macular pigment. This is a yellow substance located in the central (macular) region of the retina. Macular pigment is believed to be entirely of dietary origin. It is composed of the carotenoids, lutein and xeanthanin.

Research indicates that macular pigment contributes to maintaining the health of the eye in two ways. First, it has anti-oxidant properties, thereby depressing the activity of oxidative substances that are responsible for the degeneration of outer layers of the retina in elderly eyes. Second, it absorbs strongly in the short-wavelength (blue) region of the electromagnetic spectrum, which is known to be damaging to the delicate outer layers of the retina.

The macular region of the eye is prone to degeneration in older people. This condition is particularly debilitating because it affects the ability to drive, read and live a normal life. For example, some people with macular degeneration notice that straight lines in a landscape—such as telegraph poles, the sides of buildings or streets, appear wavy. Other symptoms include blurring of type or a page of print, with dark or empty spaces that may block the centre of the field of vision. Such degeneration is known as age related macular degeneration, or ARM for short. For demographic reasons associated with the aging population, the incidence of age related macular degeneration is on the increase in developed and developing countries, and the potential protective properties of macular pigment has lead to a great deal of interest in its in-vivo measurement.

The benefits of measuring macular pigment are clear. It identifies those patients who are at high risk of developing age related macular degeneration because of low macular pigment. Individuals who have low levels of macular pigment can be advised to modify their lifestyle and diet in a way that is already known to significantly reduce the risk of developing age related macular degeneration. An accurate and reliable measurement of the amount of macular pigment therefore has immense clinical and commercial potential.

In terms of the commercial exploitation, there are now many food supplements containing lutein, which is known to boost the levels of macular pigment in the retina. By measuring the amount of macular pigment from time to time, individuals taking lutein will know how much their macular pigment is increasing due to the ingestion of the lutein. The market for lutein-based products is large and increasing, especially in the United States of America, and manufacturers of the supplements are keen to encourage individuals to be aware of how their eyes are benefiting from the lutein so that they will continue to purchase the lutein-based product. A measurement that yields the amount of macular pigment quickly, accurately and consistently can aid such encouragement.

One aspect of the eye's, and in particular the retina's performance that is of particular interest is the sensitivity to temporal modulation, or 'flicker'. The human eye is highly sensitive to flicker, and the borderline between the presence and absence of flicker (the flicker threshold) can be easily identified. It is well known in the art that the eye's sensitivity to flicker decreases with age and also with the onset and development of many disease states. In particular, the flicker threshold has been used to determine the amount of macular pigment in the retina, and thus the susceptibility to, onset and progression of age related macular degeneration.

It is well known that sensitivity to temporal modulation of a target is linearly related to the luminance of the target. If two targets are superimposed in space and temporally modulated in anti-phase, the targets appear to flicker only if the luminances of the targets are different. When the relative intensities of the targets are adjusted so that flicker is absent or minimised, then the targets are defined as being of equal luminance as perceived by the eye. This observation is particularly useful when two targets of different wavelength are required to be equalised in luminance, a method called heterochromatic flicker photometry. Such a method is used to determine the amount of macular pigment in the retina.

In a conventional prior art method, the targets are lights of different colours, usually blue and green. The two colours are superimposed and are modulated in anti-phase. The frequency of the modulation is constant, and is usually 15 Hz, although other frequencies such as 10 Hz and 20 Hz have also been used. A subject viewing the superimposed lights perceives them to be flickering. The use of blue light is important as this is preferentially absorbed by the macular pigment. Thus, by comparing the absorption of the blue light in the macular and non-macular (peripheral) parts of the retina, where there is no macular pigment, information relating to the amount of macular pigment can be extracted.

The method requires the subject to view the superimposed lights in such a position that the lights are incident on the macular region of the retina. The subject then adjusts the intensity of the blue flickering light until the flicker disappears. At the point at which flickering is perceived to disappear, the subject has perceived the green and blue light as being of equal intensity.

Although the subject perceives the intensities of the lights to be equal, in reality they are (in general) not. The perceptions of the subject are used to determine properties of the subject's eye, or more specifically their retina.

At the point at which flicker disappears, a ratio of the intensity of blue light and green light is established. For the central (macular) region of the retina, the corresponding luminance of the blue light is known as the central luminance, $L_c$.

The measurement is repeated for a peripheral part of the retina, where there is no macular pigment. Since there is no macular pigment in the peripheral part of the retina, this measurement acts as a normalisation measurement. The measurement is taken, for example, at an angle of 6° from the macular region. At the point at which flicker disappears, a ratio of the intensity of blue light and green light is established. For the peripheral region of the retina, the corresponding luminance of the blue light is known as the peripheral luminance, $L_P$.

As is known in the art, an indication of the amount of macular pigment in the macular region of the retina can be derived from entering the measured central and peripheral luminances into the following formula:

$$MPOD = \text{Log}_{10}\left[\frac{L_C}{L_P}\right]$$

where $L_C$ and $L_P$ are the central and peripheral luminances, and MPOD is the optical density of macular pigment in the macular region.

Although the basic concept of this measurement method is straightforward, its actual implementation is not. This measurement for measuring flicker sensitivity relies on expensive apparatus that needs careful and repeated calibration and a professionally trained operator. Even with such highly stringent conditions, the results obtained are often prone to error and maybe misleading. Similar research studies conducted by different research groups often yield results that are inconsistent at best, with large discrepancies sometimes apparent between the results.

As well as errors inherent in the apparatus used, a wide range of errors is introduced due to each subject's different perceptions and sensitivities to the method used. For example, subjects may have different sensitivities to flicker and colour saturation, both of which will introduce errors into the results obtained from the prior art method. One suggested method of reducing errors in the prior art method is to take the average results of a plurality of measurements. While reducing the errors to a limited extent, such a multi-measurement experiment requires careful control of all physical and psychological factors. In an attempt to control such factors, a professionally trained operator is required. Clearly this is impractical and prevents the method being used on a wide scale, such as in pharmacies and even health centres. In particular, the requirement of a professionally trained operator prevents the method being used by an unskilled user, for example the patient or subject.

Although techniques such as taking the average of a plurality of measurements do result in the reduction of some errors, other errors remain. For example, when exposed to a prolonged period of continuous flicker, the eye's natural response is to adapt to this flicker. Responding to or sensing continuous flicker is energetically inefficient for the eye, and thus the flicker is 'blurred out' or, to some extent 'suppressed' by the eye. This is known as the Troxler Effect, and is widely known to those skilled in the art. The prior method, which involves exposing a subject to a continuous period of flicker, is consequently prone to errors introduced by the Troxler Effect.

SUMMARY

It is an object of the present invention to obviate or mitigate at least one of the above-mentioned disadvantages.

According to a first aspect of the present invention, there is provided a measurement apparatus for measuring a property of an eye of a subject, comprising: a target arranged to be viewed by the subject, the target comprising a first light and a second light arranged to undergo a modulation in anti-phase, the modulation decreasing from an initial modulation frequency at which an initial flicker of the first light and second light is not perceivable by the subject; and an indication device allowing the subject to indicate when a flicker is perceived, the modulation frequency at which the subject indicates that the flicker is perceived being defined as a threshold modulation frequency.

According to a second aspect of the present invention, there is provided a method of measuring a property of an eye of a subject using a measurement apparatus comprising a target arranged to be viewed by the subject, the target comprising a first light and a second light, the method comprising: while the subject is viewing the target, modulating the first light and the second light in anti-phase at an initial modulation frequency at which the subject cannot perceive flicker of the first and second light; decreasing the modulation frequency; in response to the subject perceiving the flicker of the first and second light, receiving an input to indicate a threshold modulation frequency.

According to a third aspect of the present invention, there is provided a measurement apparatus for measuring a property of an eye of a subject, comprising a target arranged to be viewed by the subject, the target comprising a first light and a second light arranged to be modulated in anti-phase, wherein the measurement apparatus is arranged to decrease the modulation from an initial modulation frequency at which a flicker of the first light and second light is not perceivable by the subject, the measurement apparatus being arranged to allow the subject to indicate when flicker is perceived, the modulation frequency at which the subject indicates that flicker is perceived being defined as a threshold modulation frequency.

The inventors have realised that by providing an apparatus and method that decreases the frequency of flicker until is it observable by a subject, while keeping the target intensities constant, errors can be reduced to a large degree. This is due to the fact that, by decreasing the flicker frequency, the present invention avoids or minimises errors associated with the Troxler Effect.

By repeating the measurement for different intensity ratios of the first and second lights, a profile of the subject's macular and peripheral sensitivity to flicker can be established. Such an approach limits the errors associated with each subject's individual sensitivities to measurements conducted at a particular frequency and/or intensity.

Furthermore, the inventors have recognised that a background level of light to which the first and second modulated lights are added is important when detecting flicker thresholds. Sensitivity to flicker varies markedly between individuals for different background levels of light, even though the relative variation in intensity of the modulated lights remains constant. For example, some subjects may only detect flicker when the lights are modulated with no added background light, say between zero and a value of 'x'. However, some subjects may have a higher sensitivity to flicker and are therefore able to detect flicker when the change of 'x' is on top of, or added to a background level of light. When the modulated lights are added to a background light, they are often referred to as being not as pure, or as being paler. Variation in this background level can take account of an individual subject's inherent sensitivities.

The term 'decrease' (or 'decreased', 'decreasing' etc.) used herein to describe a change in modulation frequency is intended to encompass the term 'ramp down' (or 'ramped down', 'ramping down' etc.) also used herein to described a change in modulation frequency, and which is commonly used in the art to describe a decrease in the modulation frequency.

BRIEF DESCRIPTION OF THE DRAWINGS

Embodiments of the present invention will now be described, by way of example only, with reference to the accompanying drawings, in which.

It is noted that the Figures are not to scale. Identical features appearing in different Figures are given the same reference numerals.

DETAILED DESCRIPTION

Figure 1:
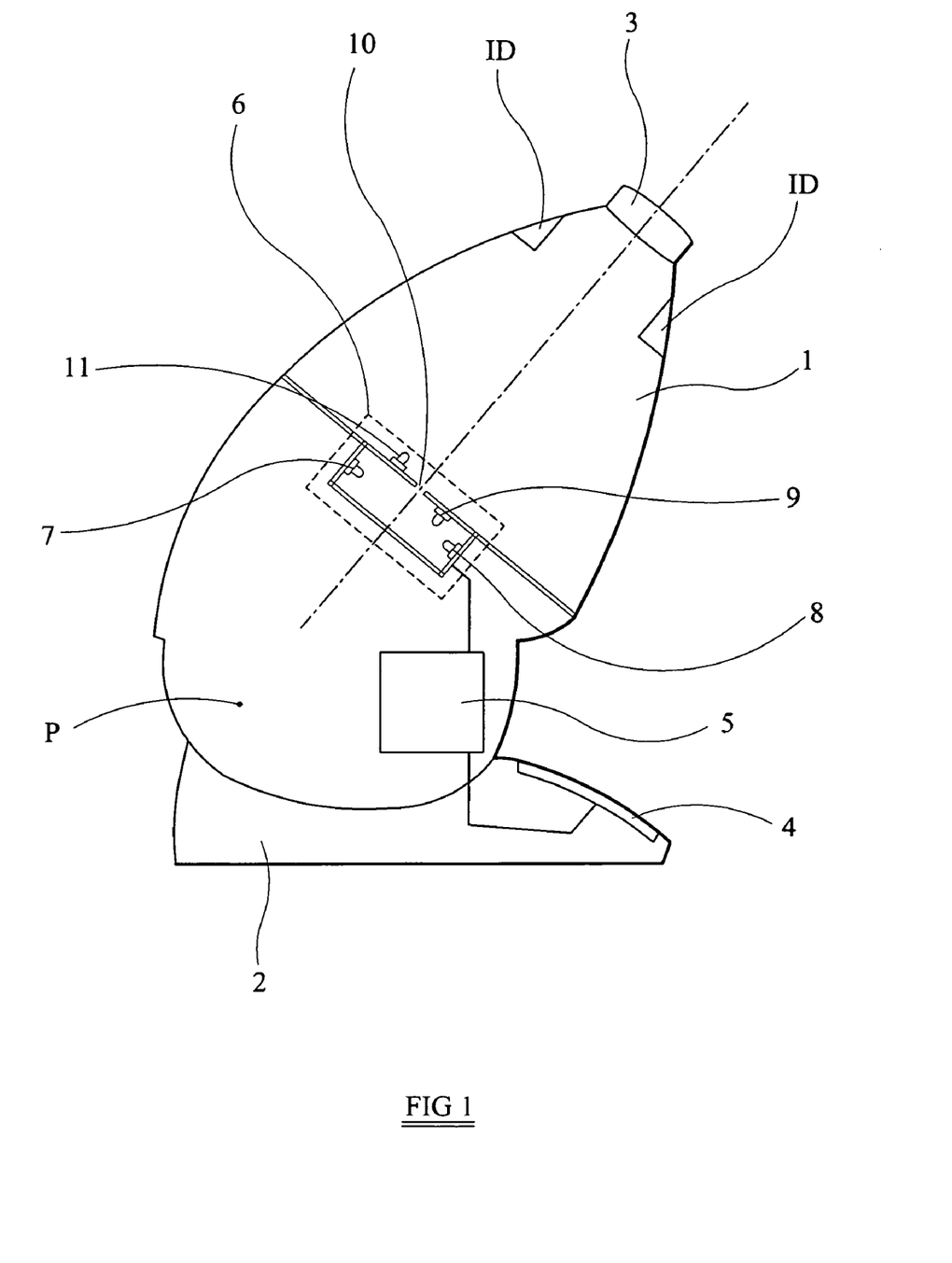
FIG. 1 is a cross-sectional view of an apparatus in accordance with an embodiment of the present invention.

FIG. 1 shows a measurement apparatus for determining the amount of macular pigment in the retina of a subject's eye. The apparatus comprises a housing 1, which is pivotably mounted on a base 2 at a pivot point P. The housing 1 includes an eyepiece 3, which permits a subject to be tested (not shown) to look inside the housing 1. The eyepiece 3 is shaped such that only one eye can look into the housing at any one time. The housing 1 and the base 2 are formed from plastic and metal mouldings. The eyepiece 3 is formed from a dense rubber material to provide a firm but comfortable support for the subject. The measurement apparatus further comprises a user interface 4 and control electronics 5.

The measurement apparatus consists of a light box 6, properties of which are controlled by the control electronics 5. The control electronics 5 are also in electrical connection with the user interface 4. The light box 6 is a plastic hollow box. The light box 6 is mounted to a plate 1a which is itself attached to an inner surface of the housing 1. The plate 1a may form part of the light box 6, for example forming one of the walls of the light box 6. The inner surface of the light box 6 is light coloured and diffusely scattering, such that it diffusely reflects light incident upon it. The system is powered by an external power supply (not shown).

Located within the light box 6 are three light emitting diodes (LEDs): a blue LED 7, a green LED 8 and a white LED 9. The blue LED 7 has a central emission wavelength of around 465 nm, whereas the green LED 8 has a central emission wavelength of around 550 nm. The white LED has a colour temperature of around 6000K. The bandwidths of the light emitted by the blue LED 7 and green LED 8 are around 20 nm.

The light box 6 further comprises an aperture 10, which is located in a side of the light box 6 that faces the eyepiece 3. The subject can view a portion of the inside of the light box 6 via the aperture 10. Looking through the aperture 10 is known as looking at the 'target'. The aperture 10 is substantially circular in cross section, and has a diameter that subtends an angle of approximately 1° with respect to the eyepiece 3. Located adjacent the aperture 10 is an LED indicator 11. The LED indicator 11 is positioned such that, when viewed from the eyepiece 3, the angle between the centre of the LED indicator 11 and the centre of the aperture 10 is approximately 6°. This angle is chosen such that two sets of measurements may be taken; one for a macular region of the subject's retina (corresponding to looking directly through the aperture 10), and one for a peripheral region of the subject's retina (corresponding to looking at the LED indicator 11, while 'paying attention' to the aperture 10). Mounted within the housing is an illumination device ID. The illumination device ID is positioned such that it is able to illuminate the side of the light box 6 that faces the eyepiece 3, i.e. the area surrounding the aperture 10.

The control electronics 5 control the experimental procedure needed to determine the amount of macular pigment in the subject's macular region.

Use of the apparatus will now be described in relation to FIGS. 1 to 7 inclusive.

Referring firstly to FIG. 1, positioning of the eyepiece 3, such that it is conveniently located for use, is achieved via manual movement of the housing 1 itself using an easily adjusted mechanical mechanism. The housing is pivoted about its pivot point P.

Figure 2:
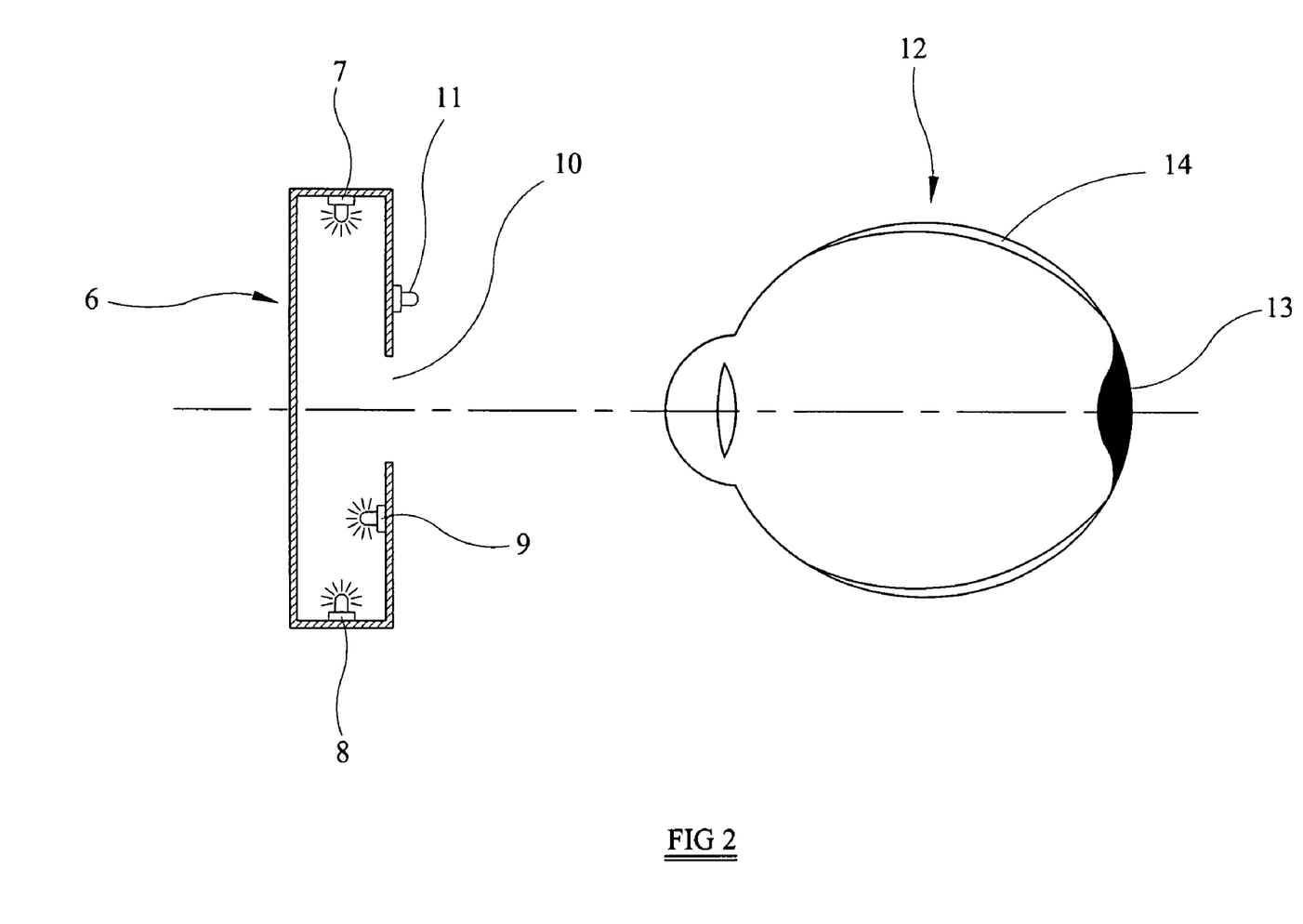
FIG. 2 is a part section view illustrating a first stage in the operation of the apparatus of FIG. 1.

In FIG. 2, a subject's eye 12 is illustrated in relation to the light box 6. The subject is made to look through the aperture 10 using one eye only, such that light emitted by the LEDs 7, 8 and 9 and transmitted through the aperture 10 is incident on the macular region 13 of the retina only i.e. not the peripheral region 14.

The illumination device ID is made to illuminate the area around the aperture 10 with a constant, non-modulating light. The illuminating light is a uniform white light, having an intensity just below a combined intensity of the light emitted by the blue LED 7, green LED 8 and white LED 9. The light serves to reduce the effect known as 'fading' of the target, when the light emitted from the target is 'suppressed' by the eye, thus giving the impression that the light emitted from the target has faded away. This effect is particularly prevalent when the light from the target impinges on a peripheral part of the subject's retina.

Figure 3:
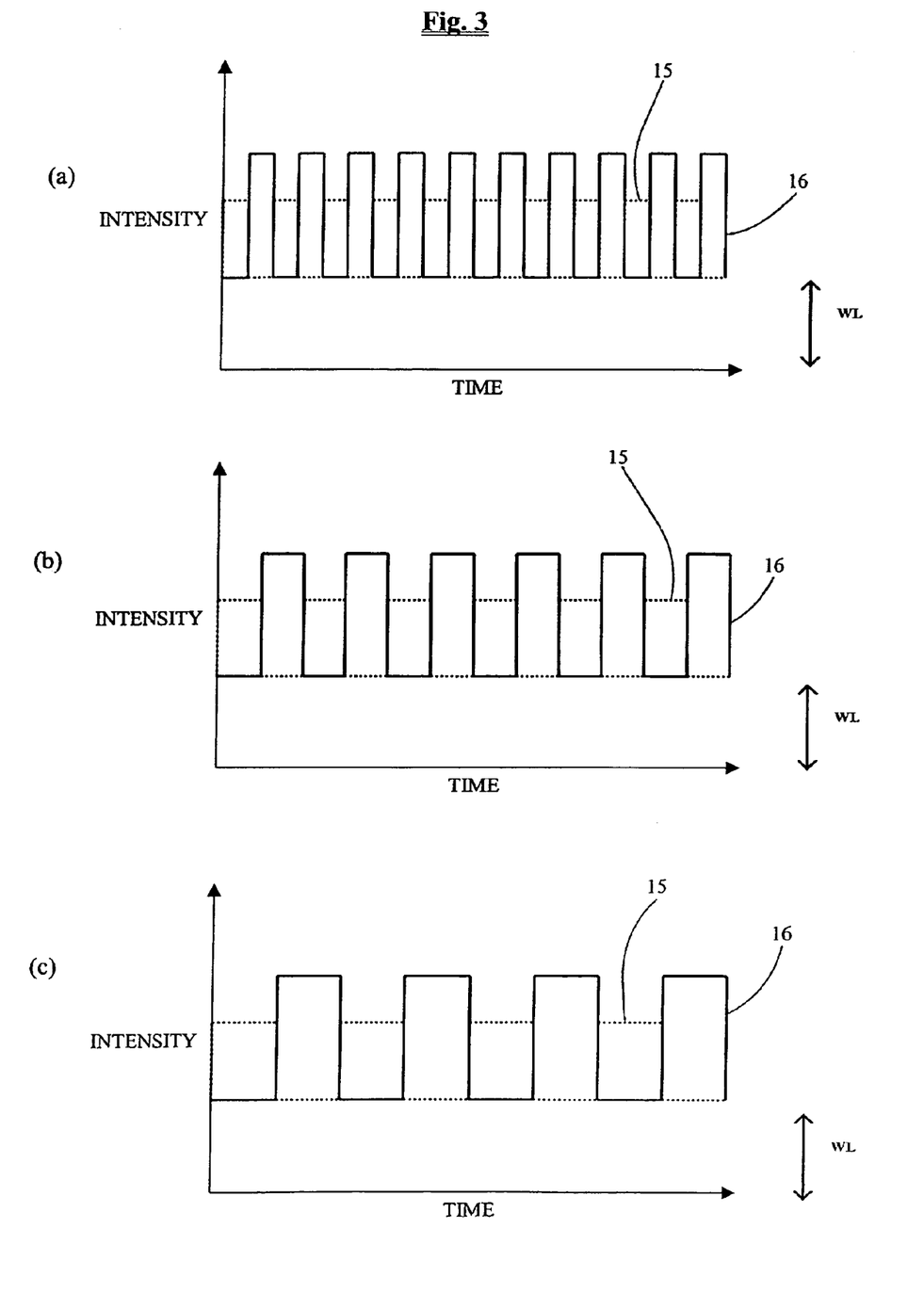
FIGS. 3 to 5 illustrate operation of an embodiment of the present invention.
Figure 4:
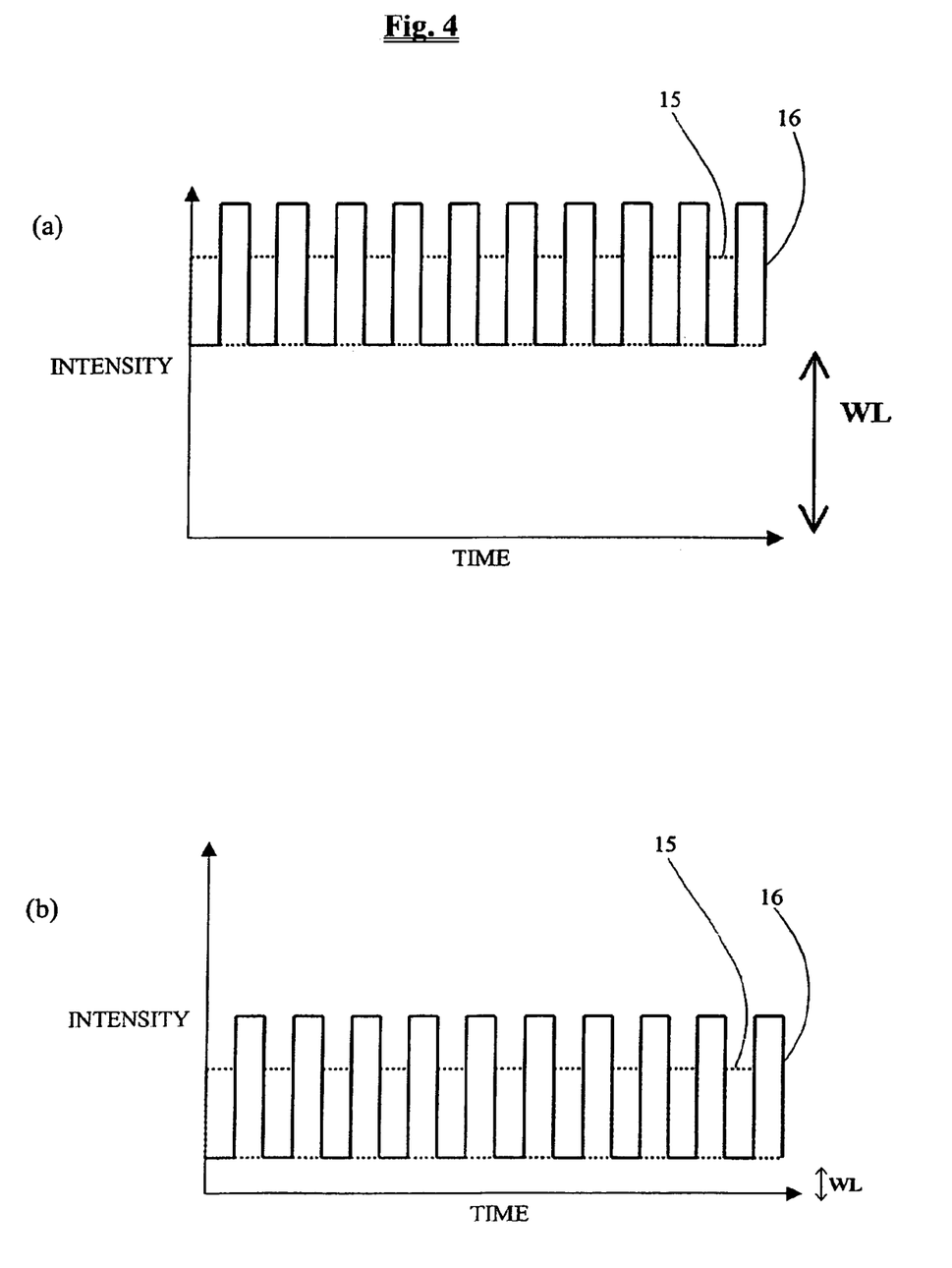
Figure 5:
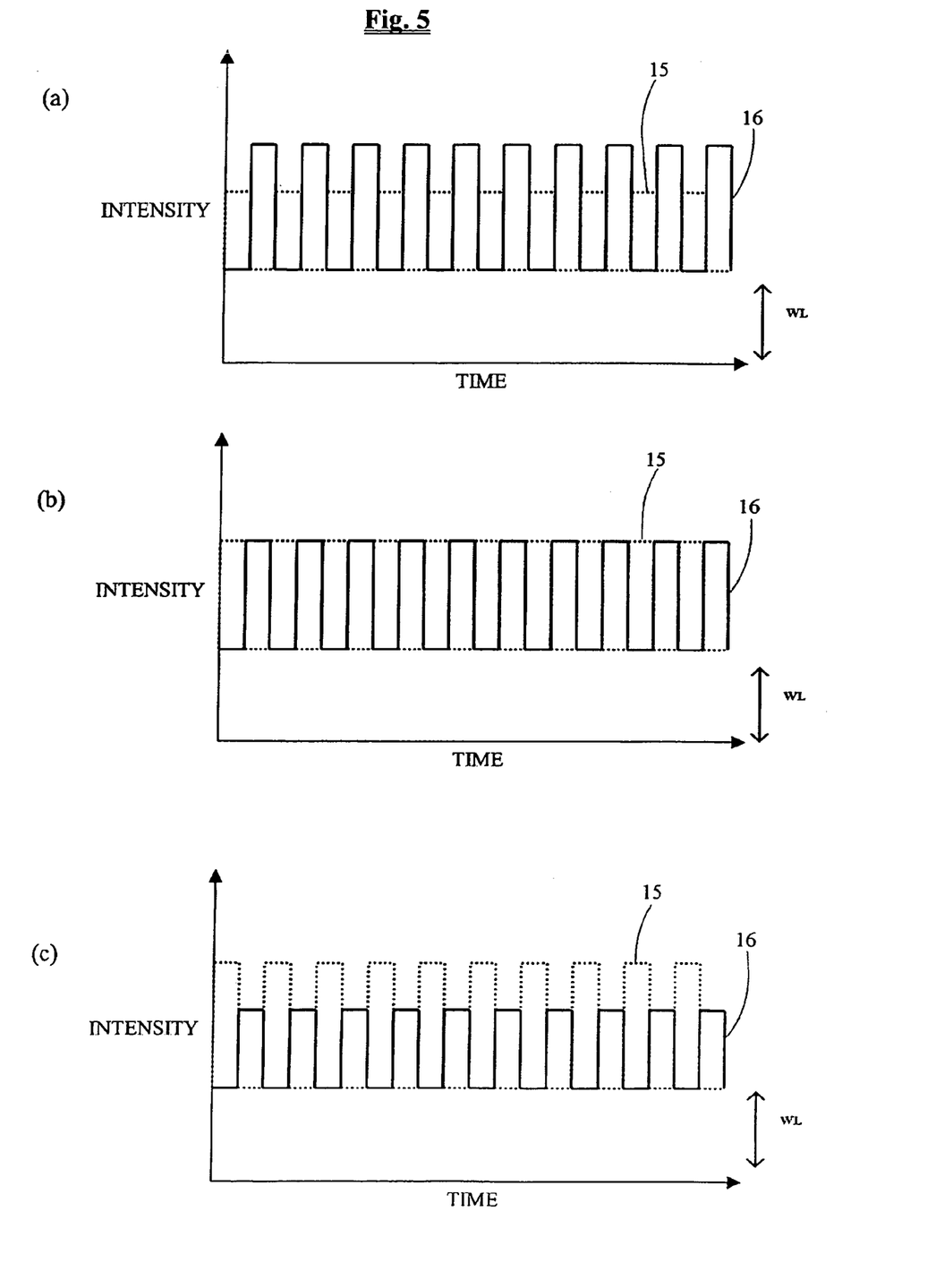

FIG. 3 shows schematically the emission profiles 15, 16, WL of the blue, green and white LEDs 7, 8, 9. FIG. 3a illustrates that the blue and green LEDs 7,8 are modulated in anti-phase, as can be seen from the green LED 8 emission profile 15 and blue LED 7 emission profile 16. In other words, the period of emission of the blue LED 7 corresponds to the period of non-emission of the green LED 8, and vice versa. It can be seen that the emission WL of the white LED 9 is not modulated, and the white LED 9 therefore provides a constant background WL upon which the light emitted 15,16 by the blue and green LEDs 7, 8 is modulated (or 'added'). Referring back to FIG. 2, since the inner surface of the light box 6 is coated with a diffuse reflector, when looking through the aperture, or at the 'target', the subject sees a uniform light, i.e. there are no bright spots or dull patches.

An initial sensitivity calibration is undertaken for the macular region of the retina 13, the purpose of which is to ensure that the experiment is conducted at the optimum sensitivity of the subject. Initially, the blue LED 7 is made to emit a higher intensity light than that of the green LED 8, as can be seen from the green LED 8 emission profile 15 and blue LED 7 emission profile 16 of FIG. 3a. The initial modulation frequency of the blue and green LED's 7,8 emission profiles 15,16 is intended to be too high for the subject to detect any flicker, i.e. the lights appear static. The initial modulation frequency is about 55 Hz. The modulation frequency is gradually reduced at about 5 Hz per second until flicker becomes detectable by the subject i.e. the 'flicker threshold' or threshold modulation frequency, is reached. This reduction in frequency is illustrated in FIGS. 3a through 3c. When the subject perceives flicker, he/she responds by pressing a button on the user interface 4. The ratio of blue to green light is then recorded, as is the frequency of modulation. The time taken for the subject to perceive flicker, thereby determining their flicker threshold for each ratio of blue to green light, typically takes a few seconds.

It is known that above a modulation frequency of 55 Hz, it is more or less impossible for a subject to perceive flicker at the combined intensities of emitted light used in this embodiment (e.g. 200 cd/m$^2$). To avoid prolonged periods when the lights are not modulating, it is desirable that the modulation frequency does not decrease far below a value of 5 Hz. Thus, it is desirable that flicker detection by the subject occurs somewhere in between these values, for example around 40 Hz.

If the subject perceives flicker at a frequency substantially above 40 Hz, they have a high flicker sensitivity. In this case, the apparatus automatically performs an adjustment such that it is made more difficult for the subject to detect flicker. This is achieved by increasing the background white level WL, to make the modulated blue and green lights paler, or not as pure. This is illustrated in FIG. 4a. The subject then detects flicker at a lower frequency, which is desirable for experimental purposes.

If the subject perceives flicker at a frequency substantially below 40 Hz, they have a low flicker sensitivity. In this case, the apparatus automatically performs an adjustment such that it is made easier for the subject to detect flicker. This is achieved by decreasing the background white level WL, to make the modulated blue and green lights purer, or not as pale. This is illustrated in FIG. 4b. The subject then detects flicker at a higher frequency, which is desirable for experimental purposes.

The automatic process of varying the background white level WL is repeated until the subject's detection of flicker is sufficiently close to, or 'around' 40 Hz. For example, this may be 40 Hz±3 Hz. This may take 3-5 iterations of the process, depending on the subject's response. Once a suitable background white level has been established, it is kept constant throughout the remainder of the experiment. The determination of the amount of macular pigment in the subject's retina then begins.

The determination of the subject's flicker threshold is performed for a series of different intensity ratios of blue and green lights while keeping the mean light intensity emitted from the combined lights substantially constant (e.g. at a value of about 200 cd/m$^2$). This is illustrated in FIGS. 5a to 5c, where the emission profile 16 of the blue LED 7 reduces in intensity through FIGS. 5a to 5c, and the emission profile 15 of the green LED 8 increases in intensity through FIGS. 5a to 5c. In other words, while the intensity of the light emitted from the blue LED 7 and green LED 8 is varied by the control electronics 5, the control electronics 5 also ensure that the combined emission intensity of the blue and green LEDs 7,8 remains substantially constant. It is noted that while the intensities of the blue and green lights are varied, the background white level, WL, remains unchanged.

Figure 7:
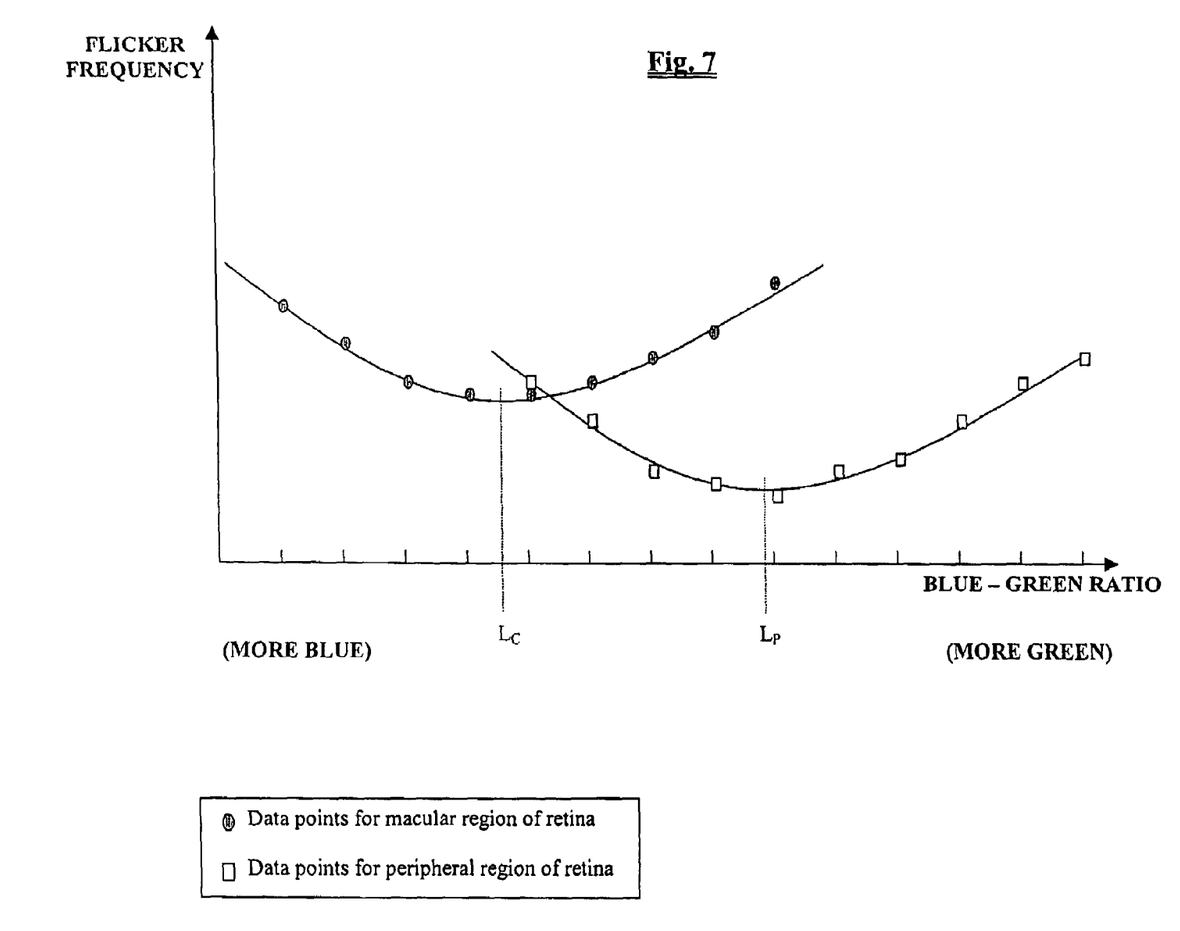
FIG. 7 is a graph representative of intermediate results obtained with the apparatus of FIG. 1.

For different intensity ratios of the lights emitted from the blue and green LEDs 7,8 the modulation frequency of the light emitted from the blue and green LEDs 7,8 is ramped down from an initial frequency, where the subject cannot perceive any flicker, to a frequency where the subject can perceive flicker i.e. the threshold frequency, or flicker threshold. At this point, the subject responds by pressing a button on the user interface 4. The modulation frequency and intensity of the light emitted from the blue and green LEDs 7,8 is recorded, and are represented by the data points in the graph of FIG. 7. FIG. 7 is described in more detail later.

At a particular intensity ratio, a minimum flicker rate is reached and at this point the lights are defined as being of equal luminance i.e. after this point, varying the intensity ratio of blue to green light causes the flicker threshold to increase. The minimum flicker rates correspond to the minima of the curves of FIG. 7. When the equal luminance point is established, the modulation is terminated. In essence the observer has determined the equal-luminance point for the green and blue lights for the macular region 13 ($L_C$), or for 'central fixation'.

The fact that the frequency is ramped down is crucial. This reduces the errors otherwise introduced by the Troxler Effect. The Troxler Effect is, as described above, known to affect measurements that depend on presenting a detectable flicker frequency to the subject for a prolonged period, while the subject varies the intensity of modulated light to detect their flicker threshold. The present invention takes the opposite approach to this prior art method, i.e. a prolonged period of flicker is not presented to the subject. Instead, in the present invention, the target, or lights thereof are initially modulated at a frequency at which the subject cannot perceive flicker, and then the modulation is ramped down until flicker is perceived. As the subject is not exposed to, or presented with a prolonged period of flicker, the present invention, at the very least, reduces experimental errors associated with the Troxler Effect.

After the equal-luminance point $L_C$ for the macular region 13 has been determined, the control electronics 5 emits an audible sound. After a small delay, the LED indicator 11 is made to emit light. The sound, and light emitting LED indicator 11 act to instruct the subject to focus on the LED indicator 11, which, as described above is 6° to one side of the aperture 10.

Figure 6:
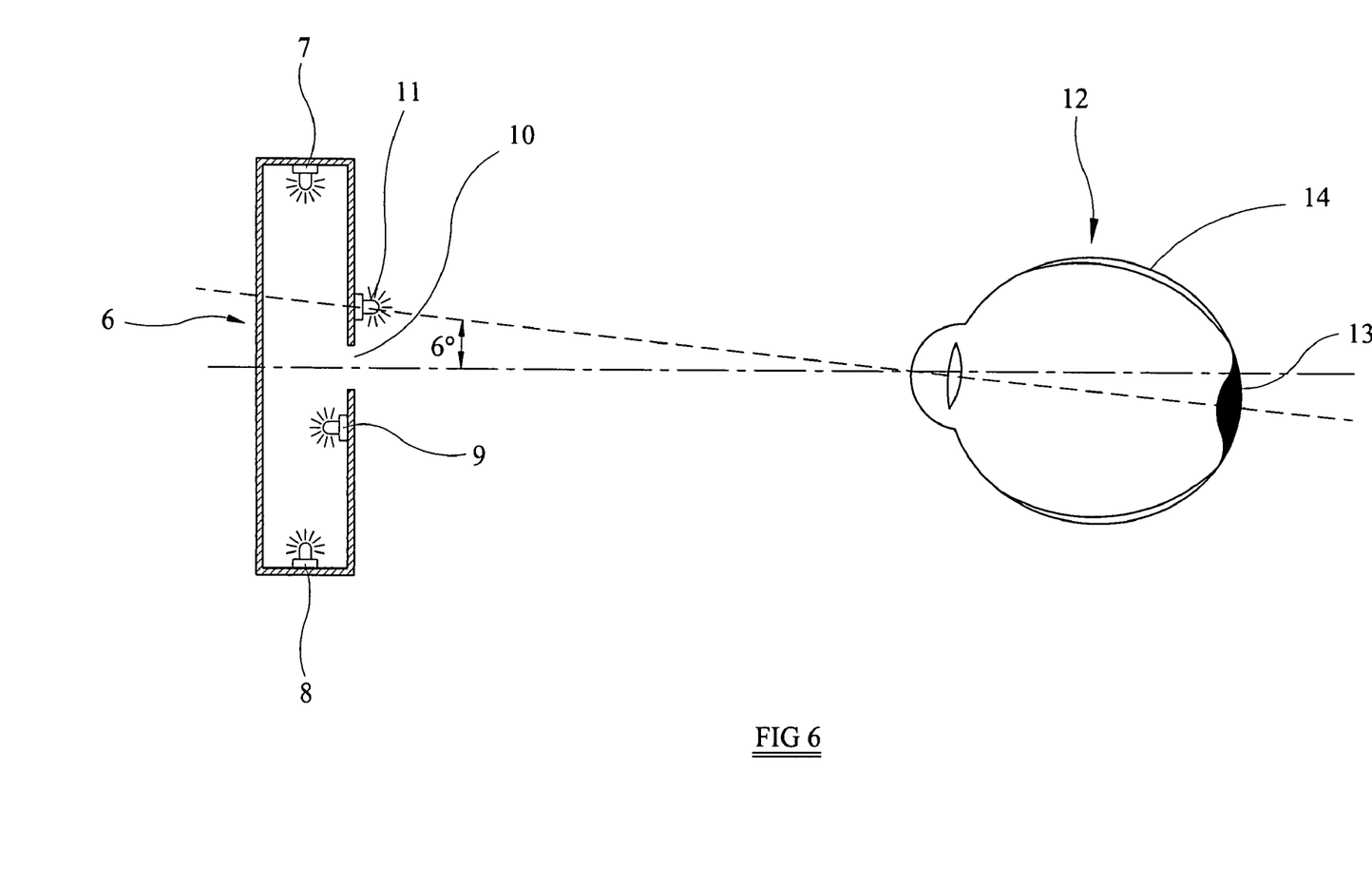
FIG. 6 is a part section view illustrating a second stage in the operation of the apparatus of FIG. 1.

FIG. 6 shows the subject's eye 12 in relation to the light box 6. The subject is made to look at the LED indicator 11, such that light emitted by the blue, green and white LEDs 7, 8, 9 and transmitted through the aperture 10 is incident on the peripheral region 14 of the retina only i.e. not the macular region 13.

Whilst the subject is looking at the LED indicator 11, the above-mentioned anti-phase modulation and intensity variation of the light emitted from the blue and green LEDs 7,8 is repeated. Specifically, an initial peripheral sensitivity calibration is undertaken, followed by the determination of the equal luminance point. As above, the modulation frequency of the light emitted from the blue and green LEDs 7,8 is ramped down from an initial frequency, where the subject cannot perceive any flicker, to a frequency where the subject can perceive flicker i.e. the threshold frequency, or flicker threshold. At this point, the subject responds by pressing a button on the user interface 4. The modulation frequency and intensity of the light emitted from the blue and green LEDs 7,8 is recorded, and then the ramping down is repeated for a different ratio of blue to green light. In this way the observer obtains the equal-luminance point for peripheral viewing $L_P$.

FIG. 7 is now referred to. The vertical axis of the graph of FIG. 7 is temporal frequency of flicker and the horizontal axis is the ratio of blue to green mean luminance. Each data point is obtained following a button press from the subject. As can be seen, the equal luminance points $L_C$, $L_P$, are minima in the data curves for the macular 13 and peripheral regions 14 respectively. It can be seen that the blue to green ratio is lower for $L_P$ than for $L_C$. This is because there is no macular pigment in the peripheral region (which absorbs blue light), and therefore less blue light is required for the subject to perceive the blue and green lights as being of equal luminance.

As described above, since there is no macular pigment in the peripheral region 14 of the retina, the equal-luminance point for peripheral viewing $L_P$ acts as a normalisation, or baseline against which the equal-luminance point $L_C$ for the macular region 13 is compared.

As stated on page 5 above, the optical density of macular pigment in the macular region 13 of the retina is derivable from the following equation.

$$MPOD = \text{Log}_{10}\left[\frac{L_C}{L_P}\right]$$

where $L_C$ and $L_P$ are the central and peripheral equal luminance points respectively, and MPOD is optical density of macular pigment in the macular region.

The present invention provides the advantage that, by determining equal luminance points $L_C$, $L_P$, in the aforementioned manner, and over a range of intensity ratios, errors previously introduced due to individual subject's sensitivity to modulation frequency and background light levels are reduced. It also has the advantage that the overall luminance is constant during the measurement of the amount of macular pigment, thereby not introducing another variable into the experiment. By taking measurements across a range of frequency and intensity ratios, generating data curves and taking the minima thereof, the frequency, intensity and background light level dependence of the measurement is greatly reduced.

The control electronics 5 control the output intensities of the green blue and white LEDs 7,8,9 as well as the periods for which they emit light. Furthermore, the control electronics 5 direct the eye of a user to a particular location, such that different parts of the retina may be non-intrusively probed. The control electronics 5 also serve to record results, and to determine the amount of macular pigment in the retina. In essence, the entire process of determining the amount of macular pigment is automated. The only input from the subject is to turn the apparatus on and off, and to indicate when they have perceived the presence, or indeed absence of a particular stimulus such as flicker of the light emitted by the blue and green LEDs 7,8. The control electronics may also allow communication with a computer for downloading of (previously stored) data, and for analysis of results from large populations. A single set of control electronics may be used to control the apparatus. Alternatively, a set of control electronics may be used for only one or more tasks. For example, a set of control electronics may be used to control the output intensities of the lights, whereas another set of control electronics may be used to control the decrease in the modulation frequency.

It will be appreciated by the skilled person that the aforementioned embodiments have been described by way of example only. The skilled person will appreciate that various modifications may be made to the aforementioned method and apparatus, while not detracting from the invention, which is defined by the claims that follow.

At a fundamental level, the method and apparatus has been described in relation to the determination of macular pigment in a single eye. It will be clear that the determination can be undertaken for any number of eyes, for example by taking each one in turn.

The 'target' that is viewed by the subject has been described thus far as looking through or 'at' the aperture 10. However, the target may have other guises. For example, the target may comprise an image of lights projected onto a screen. Alternatively, the targets may be the actual lights. For example, the lights may be grouped in close proximity such that the light emitted therefrom appears to be superimposed.

In the embodiments described above, the modulation frequency has been described as being ramped down linearly, i.e. the modulation frequency is decreased at a constant rate. However, it will be appreciated that the modulation frequency can have different ramp down profiles. For example, the modulation frequency may be decreased logarithmically, or non-linearly. The modulation frequency may be decreased in a stepwise manner. In a stepwise manner, the subject will have time to determine whether the modulated light is flickering or not. The modulation frequency may be ramped down linearly at a rate other than 5 Hz per second. For example, the modulation frequency may be ramped down at a rate of between 3 Hz per second and 7 Hz per second.

It will be appreciated that the accurate determination of the amount of macular pigment using the present invention is based on the assumption that the part of the retina underlying the macular pigment, i.e. the macular region 13, has the same spectral characteristics as the peripheral region 14, i.e. that measured differences in the blue-green ratio for a given subject are due to the presence or absence of the macular pigment. It is known that various types of photoreceptors are distributed fairly uniformly across the central part of the retina (where the measurements take place), but that some are not. For example, it is known that photoreceptors known as 'rods' and 'short-wavelength cones' are distributed fairly non-uniformly across this same region. Thus, it is necessary to avoid the short wavelength cones and rods introducing errors into the measurements.

Avoiding the short wavelength cones and rods introducing errors into the measurements can be achieved by selecting light which reduces the sensitivity of rods and short wavelength cones to a negligible level. For example, lights having an intensity greater than 80 $cd/m^2$, and a colour temperature of 7000K may be sufficient. It will be appreciated that other intensities and colour temperatures are suitable, the choice of which may have as their aim the minimisation or avoidance of detection by non-uniformly located photoreceptors.

It will be appreciated that the illumination device ID, which is illustrated in FIG. 1, may be a simple light bulb. The illumination device ID may be a more complex piece of apparatus. There may be a pattern on the area surrounding the target, or aperture 10 and this may be projected. Such a pattern may (further) reduce undesirable effects, such as 'fading'. It will be appreciated that the illumination device ID need not emit white light. For example, the illumination device ID need only emit light that results in an improved experimental apparatus. Such a light may have the same wavelength as that of the modulated lights. The light emitted by the illumination device ID may (further) reduce detrimental effects such as 'fading'. For example, and most preferably, the light emitted by the illumination device ID has an intensity slightly lower than the combined intensity of the light emitted from the target. For example, the intensity may be less than or equal to 200 cd/m². The surface of the light box 6 may be treated so as to have an effect on the light emitted by the illumination device ID. For example, the surface may reduce reflections, such that the subject sees a 'matt' light surrounding the target. This may (further) reduce detrimental effects such as 'fading'.

It will be appreciated that the use of green light is not essential, but preferred. Similarly, it will be appreciated that the use of blue light is not essential, but preferred. Blue light is preferred because this has a wavelength that is most strongly absorbed by the macular pigment, the pigment most strongly absorbing at 460 nm. 'Blue' light may be in the range of 410 to 510 nm. Green light is preferred as the light to be in anti-phase with the blue light because this has a wavelength which is least strongly absorbed by the macular pigment, the pigment least strongly absorbing at wavelengths longer than 520 nm. Thus it will be appreciated that light other than green, and having a longer wavelength than 520 nm may also be suitable. The green-blue combination is the most preferable combination. Due to the blue light being the most strongly absorbed and the green light being the least strongly absorbed, the blue-green combination affords the greatest signal to noise ratio for the measurement.

In the embodiment described above, the mean intensities of the blue and green lights have been controlled by the control electronics, such that, while the ratio of blue to green light is made to vary, the overall intensity is kept constant. This has the advantage of maintaining the adaptation level of the photoreceptors constant throughout the measurement sequence, i.e. the photoreceptors do not have to constantly adjust to the intensity of light, which is energetically unfavourable, and may introduce Troxler Effects. However, it will be appreciated that keeping the overall intensity constant is not essential.

In the embodiment described above, the intensity ratio of blue to green light is varied by increasing the intensity of green light, while simultaneously reducing the intensity of blue light. It will be appreciated that the ratios may be varied in other ways, for example, the intensity ratio of blue to green light may be varied by increasing the intensity of blue light, while simultaneously reducing the intensity of green light.

It has been stated above that a second set of measurements is taken when the subject is made to look at an LED indicator or fixation point 11 that is located at an angle of 6° from the aperture 10. It will be appreciated that it is not essential that the angle is 6°. The second set of measurements should be taken in a region adjacent to the macular region 13, where no pigment is present. For example, the LED indicator 11 may be located at an angle greater than or equal to 6° from the aperture 10. For example, the angle may be 8° from the aperture 10. Alternatively, the LED indicator 11 may be located at an angle less than or equal to 6° from the aperture 10. The LED indicator may be moveable to account for the different extent or spatial characteristics of macular pigment within a different subject's retina. An indication of whether or not the peripheral measurement has been taken in a suitable region may be derived from the value of $L_P$, which will be a higher blue-green ratio when macular pigment is present.

Although it has been stated that the subject should move his/her eyes in order to stimulate the peripheral region of the retina 14, this method is not essential. Peripheral presentation of the target may be realised by using the target or aperture 10 as a fixation point and causing a second target to flicker at 6°, or whatever eccentricity is deemed appropriate. This peripheral stimulus could be one, two, three or four annular segments, located above, below and either side of the centre respectively. Each annular segment may be centred on, and surround the target.

Emissive devices have been described as being LEDs. It will be appreciated that although preferable, the use of LEDs is not essential. All that is required is for the lights modulated in anti-phase to be perceived as different colours by the subject. Ideally, the intensity of the lights and the temporal emission frequency can be easily varied (for example, from 5 Hz to 55 Hz). LEDs are preferable, as they satisfy these conditions. However, it will be appreciated that other lights sources such as organic LEDs or spectrometers may be suitable. In the embodiments described above, single LEDs have been described as providing the green, blue and white light. It will be appreciated that more than one LED, or light source, may provide a particular light. For example, the apparatus may comprise three green LEDs, three blue LEDs and three white LEDs. The light sources may be spatially grouped by colour or function, or evenly distributed within the light box 6.

In the embodiments described above, the sensitivity calibration has been carried out using a preferred flicker threshold detection of 40 Hz. It will be appreciated that depending on the requirements of the experiment, the desired frequency may be different than 40 Hz. For example, the preferred flicker threshold frequency may be in the range of 20 Hz to 45 Hz. The preferred flicker threshold frequency may be 35 Hz. The experiment to determine the amount of macular pigment in the retina of a subject may proceed when this target is reached, or after a predetermined number of iterations.

The initial calibration serves to 'sharpen' the data curves illustrated in FIG. 7, so that a minimum is more readily identifiable. A calibration may be replaced by taking a larger number of measurements as the minimum is approached, or by accurate modelling of the results.

The background level WL (see, for example, FIG. 3*a*) has been described as being white light. It will be appreciated that the background level may be other colours. It is desirable to have the first light and second light varying from a zero to a non-zero emission intensity, and superimposing (or adding) these onto a steady background. This allows for more accurate control of both the background level and the modulated lights. It will however be appreciated that the background level could be provided by one or both of the modulated lights. In this case, the emission of one or both of the lights would vary from a non-zero background level to a high level, and so on.

The user interface 4 may be local to the apparatus. For example, the user interface 4 may be part of the apparatus. It will be appreciated that the user interface 4 may be remote from the apparatus. For example, the user interface may be connected to the measurement apparatus by a wire, or a wire free link (e.g. infra-red or radio waves). The subject may respond to the detection of flicker by the press of a button. However, the user may respond to the detection of flicker by providing a different input, i.e. the user may provide an input to the apparatus using any suitable indication device. For example, the input may be a verbal or non-verbal input. The detection of a verbal input to the apparatus may be facilitated by the use of a microphone, together with crude or advanced voice recognition software. The microphone may be part of the user interface 4. In general terms, it will be appreciated that the input from the user to the measurement apparatus may be direct or may be indirect.

It will be further appreciated that the user interface 4 may also display the results of the test to a subject, either graphically or in text form. The results may be displayed via a separate piece of apparatus, such as an attached screen or printer. The results may be quantitative scientific values or data, or qualitative advice. For example, the results may indicate a density of macular pigment, which is useful for a doctor or pharmacist. Alternatively, or in combination, the results may simply give general advice such as the general health of the subject's eye. Alternatively or in combination, the advice may comprise dietary suggestions, such as to increase the amount of a particular foodstuff or supplement in the subject's diet. The results may be accompanied by advice regarding where to obtain this foodstuff or supplement.

The invention claimed is:

1. A measurement apparatus for measuring a property of an eye of a subject, comprising:
    a target arranged to be viewed by the subject, the target comprising a first light and a second light arranged to undergo a modulation in anti-phase, the modulation decreasing from an initial modulation frequency at which an initial flicker of the first light and second light is not perceivable by the subject; and
    an indication device allowing the subject to indicate when a flicker is perceived, the modulation frequency at which the subject indicates that the flicker is perceived being defined as a threshold modulation frequency.

2. The measurement apparatus of claim 1, wherein the decreasing of the modulation frequency is stopped when the subject indicates that the flicker is perceived.

3. The measurement apparatus of claim 1, wherein the modulation frequency is decreased at a linear rate.

4. The measurement apparatus of claim 3, wherein the modulation frequency is decreased at a rate of between 3 Hz per second and 7 Hz per second.

5. The measurement apparatus of claim 4, wherein the modulation frequency is decreased at a rate of 5 Hz per second.

6. The measurement apparatus of claim 1, wherein the modulation frequency is decreased from a frequency of less than or equal to 55 Hz, to a frequency of greater than or equal to 5 Hz.

7. The measurement apparatus of claim 1, further comprising control electronics arranged to control the decrease of the initial modulation frequency.

8. The measurement apparatus of claim 7, wherein the control electronics are arranged to control an intensity of the first light and an intensity of the second light.

9. The measurement apparatus of claim 8, wherein the control electronics are arranged to change the intensity of the first light after the threshold modulation frequency has been defined, and to then repeat the decrease of the modulation frequency.

10. The measurement apparatus of claim 1, wherein the target further comprises a background light source arranged to provide a non-modulated background light.

11. The measurement apparatus of claim 10, wherein the background light source is a third light.

12. The measurement apparatus of claim 1, further comprising an indicator, the indicator being located remote from the target such that, when the indicator is viewed by the subject, the first light and the second light impinge on a peripheral region of the subject's retina.

13. The measurement apparatus of claim 12, wherein the indicator is moveable.

14. The measurement apparatus of claim 12, wherein the indicator is greater than or equal to 6 degrees away from the target, from the perspective of the subject.

15. The measurement apparatus of claim 1, further comprising an illumination device arranged to illuminate an area around the target.

16. The measurement apparatus of claim 15, wherein the illumination device comprises projection means arranged to project one of an array of dots or a grid onto an area around the target.

17. The measurement apparatus of claim 1, wherein the indication device is a direct input or an indirect input device operated by the subject when the subject perceives the flicker.

18. A method of measuring a property of an eye of a subject using a measurement apparatus comprising a target arranged to be viewed by the subject, the target comprising a first light and a second light, the method comprising:
    while the subject is viewing the target, modulating the first light and the second light in anti-phase at an initial modulation frequency at which the subject cannot perceive flicker of the first and second light;
    decreasing the modulation frequency;
    in response to the subject perceiving the flicker of the first and second light, receiving an input to indicate a threshold modulation frequency.

19. The method of claim 18, wherein the method further comprises recording an intensity of the first light at the threshold modulation frequency.

20. The method of claim 19, further comprising repeating the method for a different intensity of the first light.

21. The method of claim 20, wherein, for each repetition, the first light has a lower intensity.

22. The method of claim 21, wherein, for each repetition, the second light has a higher intensity.

23. The method of claim 20, wherein, for each repetition, the combined intensity of the first light and second light is substantially fixed.

24. The method of claim 18, wherein the subject looks directly at the target, so that the first light and the second light are incident on a macular region of a retina of the subject's eye.

25. The method of claim 18, wherein the subject looks at an indicator, so that the first light and the second light are incident on a peripheral region of a retina of the subject's eye.

26. The method of claim 18, wherein the method is repeated for a plurality of different intensities of the first light, thereby yielding a plurality of threshold modulation frequencies, and wherein a lowest threshold modulation frequency is determined, together with the ratio of the intensity of the first light and the second light at that lowest threshold modulation frequency.

27. The method of claim 26, wherein the method is performed for light incident on the macular region of the subject's retina, establishing a lowest threshold modulation frequency and corresponding intensity ratio for the macular region, and the method is then repeated for light incident on the peripheral region of the subject's retina, establishing a lowest threshold modulation frequency and corresponding intensity ratio for the peripheral region.

28. The method of claim 27, wherein the intensity ratio determined for the macular region is compared with the intensity ratio determined for the peripheral region, to derive an indication of the amount of macular pigment in the retina of the subject's eye.

29. The method of claim 18, further comprising:
    providing a non-modulated background light to which the first and second modulated lights are added;

repeating the method until the threshold modulation frequency is a preferred frequency, setting the intensity of the non-modulated background light to a new level on each repetition.

30. The method of claim 29, wherein the preferred frequency is in the range of 20 Hz to 45 Hz.

31. The method of claim 30, wherein the preferred frequency is 40 Hz.

32. The method of claim 18, wherein the modulating and the decreasing is automatically controlled by control electronics.

33. The method of claim 18, wherein the decreasing of the modulation frequency is stopped when the subject provides the input to the measurement apparatus.

34. The method of claim 18, wherein the input is a direct input.

35. The method of claim 18, further comprising recording the threshold modulation frequency, the threshold modulation frequency being indicative of the property of the eye of the subject.

36. A measurement apparatus for measuring a property of an eye of a subject, comprising a target arranged to be viewed by the subject, the target comprising a first light and a second light arranged to be modulated in anti-phase, wherein the measurement apparatus is arranged to decrease the modulation from an initial modulation frequency at which a flicker of the first light and second light is not perceivable by the subject, the measurement apparatus being arranged to allow the subject to indicate when flicker is perceived, the modulation frequency at which the subject indicates that flicker is perceived being defined as a threshold modulation frequency.

\* \* \* \* \*